United States Patent [19]
Mohr et al.

[11] Patent Number: 5,437,695
[45] Date of Patent: Aug. 1, 1995

[54] FUELS AND LUBRICANTS CONTAINING N-ALKYLCARBOXAMIDES

[75] Inventors: Juergen Mohr, Gruenstadt; Knut Oppenlaender, Ludwigshafen; Hans J. Pander, Roedersheim-Gronau; Rolf Schneider, Mannheim; Juergen Thomas, Fussgoenheim; Peter Schreyer, Weinheim, all of Germany

[73] Assignee: BASF Aktiengesellschaft, Ludwigshafen, Germany

[21] Appl. No.: 47,300

[22] Filed: Apr. 19, 1993

[30] Foreign Application Priority Data

Apr. 25, 1992 [DE] Germany ............. 42 13 677.6

[51] Int. Cl.⁶ .............................. C10L 1/22
[52] U.S. Cl. .............................. 44/418
[58] Field of Search ...................... 44/418

[56] References Cited

U.S. PATENT DOCUMENTS

| | | | |
|---|---|---|---|
| 3,338,967 | 8/1967 | Potts et al. | 260/583 |
| 3,530,153 | 9/1970 | Potts et al. | 260/404 |
| 3,756,793 | 9/1973 | Robinson . | |
| 3,996,024 | 12/1976 | Coon et al. | 44/71 |
| 4,044,039 | 8/1977 | DeVries . | |
| 4,743,389 | 5/1988 | Braid et al. | 252/51.5 A |
| 4,832,702 | 5/1989 | Kummer et al. . | |

FOREIGN PATENT DOCUMENTS

| | | |
|---|---|---|
| 2050967 | 3/1992 | Canada . |
| 355895 | 2/1990 | European Pat. Off. . |
| 1405652 | 9/1975 | United Kingdom . |

OTHER PUBLICATIONS

Org. React. 17 (1969), 213-325 month unknown.

*Primary Examiner*—Prince Willis, Jr.
*Assistant Examiner*—Cephia D. Toomer
*Attorney, Agent, or Firm*—Keil & Weinkauf

[57] ABSTRACT

Fuels and lubricants contain, as detergents, N-alkylcarboxamides prepared from olefins by the Ritter reaction.

5 Claims, No Drawings

FUELS AND LUBRICANTS CONTAINING N-ALKYLCARBOXAMIDES

The present invention relates to fuels for internal combustion engines and lubricants containing small amounts of N-alkylcarboxamides.

The carburettor and intake system of gasoline engines, as well as injection systems for fuel metering in gasoline and diesel engines, are being increasingly contaminated by impurities due to dust particles from the air, uncombusted hydrocarbon residues from the combustion space and the crankshaft vent gases passed into the carburettor.

The residues shift the air/fuel ratio during idling and in the lower part-load range, so that the mixture becomes richer, combustion becomes more incomplete and in turn the amounts of uncombusted or partially combusted hydrocarbons in the exhaust gas become greater and the gasoline consumption increases.

It is known that, in order to avoid these disadvantages, fuel additives are used for keeping valves and carburettors or injection systems clean (cf. for example: M. Rossenbeck in Katalysatoren, Tenside, Mineralöladditive, Editors J. Falbe and U. Hasserodt, page 223 et seq., G. Thieme Verlag, Stuttgart 1978).

Depending on the mode of action and on the preferred place of action of such detergent additives, a distinction is now made between two generations.

The first generation of additives was only able to prevent the formation of deposits in the intake system but was not able to remove existing deposits, whereas the additives of the second generation can do both (keep-clean and clean-up effect), owing to their excellent heat stability, particularly in zones at relatively high temperatures, ie. at the intake valves.

The molecular structural principle of fuel detergents can in general be described as the linking of polar structures with generally relatively high molecular weight, nonpolar or lipophilic radicals.

Typical members of the second generation of additives are often products based on polyisobutenes in the nonpolar moiety. Here in turn, additives of the polyisobutylamine type are particularly noteworthy. Polyisobutylamines are obtained, starting from polyisobutenes, essentially by two processes. The first takes place via chlorination of the polymer starting material and subsequent nucleophilic substitution by amino or preferably ammonia. The disadvantage of this process is the use of chlorine and the occurrence of chlorine- or chloride-containing products which are not at all desirable and as far as possible are avoided (German Laid-Open Applications DOS 2,129,461 and DOS 2,245,918).

In the second process, a reactive polyisobutene is first carbonylated in an oxo synthesis and then subjected to hydrogenation under aminating conditions in the presence of ammonia (German Laid-Open Application 3,611,230).

German Laid-Open Application DOS 2,061,057 discloses a process for the preparation of primary amines and of corresponding formamide derivatives and formiminoesters, in which, inter alia, polyisobutylene is also subjected to a Ritter reaction to give amines.

The Ritter reaction is the reaction of olefins with HCN or nitriles under acidic catalysis to give substituted amides, which can be hydrolyzed to amines.

This reaction is described, for example, in Org. React. 17 (1969), 213–325, or in Houben-Weyl E5 (1985), pages 1032–1041 or Houben-Weyl XI/1 (1957), page 994 et seq.

The polyisobutylamines prepared according to German Laid-Open Application DOS 2,061,057 correspond to the compounds according to German Laid-Open Application DOS 2,245,918. Their use as detergents in fuels and lubricants is also mentioned in German Laid-Open Application DOS 2,061,057. According to this publication, however, it is necessary to hydrolyze the formamides initially obtained by the Ritter reaction. As in the case of German Laid-Open Applications DOS 2,245,918 and DOS 3,611,230, an effective end product is obtained from the olefin in only two stages.

Moreover, the acid required after the Ritter reaction for hydrolysis cannot be recycled to the reaction since it is contaminated with the formic acid formed in the hydrolysis. This hydrolysis therefore results in a highly undesirable acid or salt load.

It is an object of the present invention to provide highly effective detergents for fuels and lubricants, which can be prepared by a very simple process, ie. in one step, from the corresponding olefins, without producing large amounts of salt load which can no longer be utilized.

We have found that this object is achieved by fuels or lubricants containing small amounts of compounds of the formulae Ia and/or Ib

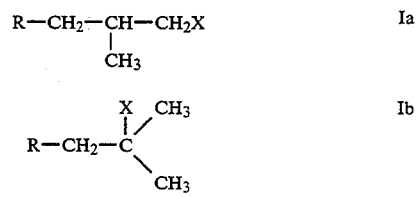

where R is an aliphatic hydrocarbon radical containing alkyl side chains and having a number average molecular weight of from 250 to 5,000, X is

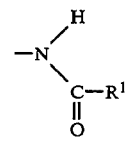

and $R^1$ is hydrogen, $C_1$–$C_6$-alkyl, phenyl or alkylphenyl of 7 to 14 carbon atoms.

Surprisingly, the N-alkylcarboxamides prepared directly by the Ritter reaction already have good activity as detergents.

A polyisobutene derived from isobutene and from 0 to 30% by weight of n-butene and having an average molecular weight of from 250 to 5,000 is preferably used as the olefin component for the Ritter reaction. Owing to the known mechanism of the Ritter reaction, it is not absolutely essential for the polyisobutene to be an α-olefin.

A preferably used nitrile component is hydrocyanic acid, ie. the particular N-polyisobutylformamides are obtained in the reaction, which is most advantageously carried out under catalysis by sulfuric acid. However, it is also possible to use nitriles, eg. acetonitrile or benzonitrile, which may be alkyl-substituted, and the total number of carbon atoms of the alkyl substituents may be 1 to 8.

The N-alkylcarboxamides are added to the fuels and lubricants in amounts having detergent activity; in particular, they are added to the fuels in amounts of from 50 to 5,000, preferably from 100 to 2,000, ppm and to the lubricating oils in amounts of from 0.5 to 10, preferably from 1 to 5, % by weight, based on the lubricating oil.

The olefins (polyalkylenes) used in the Ritter reaction for the preparation of the novel additives are prepared by polymerizing straight-chain or branched monomeric $C_2$-$C_{30}$-olefins, preferably $C_2$-$C_6$-olefins, in particular $C_2$-$C_4$-olefins, the polymerization being carried out in such a way that chain termination leads to a double bond (for example by cationic or coordinative polymerization).

1-Alkenes, in particular propylene, 1-butene, isobutene or mixtures of these olefins, are preferably used as monomeric olefins for the preparation of the starting component for the Ritter reaction.

Ethylene is used only in conjunction with comonomers, since pure polyethylene leads to compounds which are not soluble in fuels under normal conditions.

The resulting polyalkylenes may be homopolymers or copolymers, each of which have alkyl side chains of 1 to 28, preferably 1 to 4, in particular 1 or 2, carbon atoms.

The polyisobutenes preferably used as starting components for the Ritter reaction have an average molecular weight of from 500 to 5,000, in particular from 800 to 2,000. They are obtained by cationic polymerization of isobutene by a known process, a double bond remaining after termination of the polymer chain in the last monomer incorporated (cf. for example German Laid-Open Application DOS 2,702,604 and EP-A 0 145 235).

The novel additives can also be used in combination with other known detergents and dispersants in fuel additive formulations.

The conventional polyisobutylamines of the formula

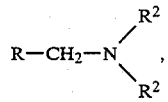

where R is a polybutyl or a polyisobutyl radical derived from isobutene and from 0 to 30% by weight of n-butene and $R^2$ is hydrogen, $C_1$-$C_{10}$-alkyl or $C_1$-$C_8$-aminoalkyl which may be substituted by further amino-carrying $C_1$-$C_6$-alkyl radicals, are particularly suitable for achieving a very good detergent effect.

Testing of the products as fuel additives, in particular of their suitability as valve and carburettor cleaners, is performed with the aid of engine tests which are carried out in a test bay with a 1.2 l Opel Kadett engine according to CEC-F-02-T-79.

EXAMPLES

1. Preparation of a polyisobutylformamide

A mixture of 200 g of concentrated sulfuric acid, 10 g of water and 32.4 g of anhydrous hydrogen cyanide is initially taken in a stirred flask.

A solution of 400 g of polyisobutene (average molecular weight 950, iodine number 27.2) in 400 g of cyclohexane is metered into this mixture in the course of 1.5 hours, the temperature being kept at from 10° to 15° C., if necessary by cooling. The viscous mixture is then stirred for a further 14 hours at about 15° C.

Thereafter, 600 g of water are added at room temperature and 30 ml of an azeotropic mixture of hydrogen cyanide, cyclohexane and water are distilled off, after which the reaction mixture is virtually free of hydrogen cyanide.

A further 500 ml of cyclohexane are added, the aqueous phase is separated off and the organic phase is washed with 3 times 500 ml of water.

After removal of the cyclohexane under reduced pressure, the product remains as a virtually colorless, viscous oil whose iodine number is still 3.8. The nitrogen content is 1.2% and the yield is accordingly from 85 to 90%.

2. Testing of the keep-clean effect for valves in the engine test

| | Deposit [mg]* Valve No. | | | |
|---|---|---|---|---|
| | 1 | 2 | 3 | 4 |
| Base value | 667 | 521 | 368 | 846 |
| Reaction product from Example 1 (800 ppm) | 13 | 8 | 0 | 11 |

*According to CEC-F-02-T-79

We claim:

1. A fuel for internal combustion engines containing amounts having detergent activity of compounds of the formula Ia or Ib

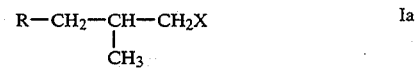

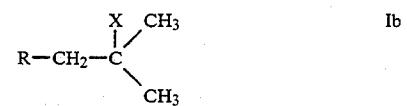

where R is an aliphatic hydrocarbon radical containing alkyl side chains and having a number average molecular weight of from about 800 to about 2,000, X is

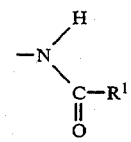

and $R^1$ is hydrogen, $C_1$-$C_6$-alkyl, phenyl or alkylphenyl of 7 to 14 carbon atoms.

2. A fuel as defined in claim 1, wherein R is a polybutyl or polyisobutyl radical derived from isobutene and from 0 to 30% by weight of n-butene.

3. A fuel as defined in claim 1, wherein $R^1$ is hydrogen.

4. A fuel as defined in claim 1, which contains from 50 to 5,000 ppm of a compound of the formula I.

5. A fuel as defined in claim 1, which contains, in addition to a compound of the formula I, a fuel detergent of the formula

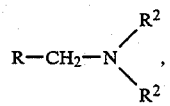

where R has the meanings stated in claim 2 and $R^2$ is hydrogen or $C_1$-$C_{10}$-alkyl or $C_1$-$C_8$-aminoalkyl which may be substituted by further amino-carrying $C_1$-$C_6$-alkyl radicals.

* * * * *

UNITED STATES PATENT AND TRADEMARK OFFICE
CERTIFICATE OF CORRECTION

PATENT NO.: 5,437,695

DATED: August 1, 1995

INVENTOR(S): MOHR et al.

It is certified that error appears in the above-identified patent and that said Letters Patent is hereby corrected as shown below:

Column 4, claim 5, line 65, "$C_1$-$C_{10}$-alkyi" should read --$C_1$-$C_{10}$-alkyl--.

Signed and Sealed this

Fourth Day of March, 1997

*Attest:*

*Attesting Officer*

BRUCE LEHMAN

*Commissioner of Patents and Trademarks*